United States Patent [19]
Kyotani

[11] Patent Number: 4,690,642
[45] Date of Patent: Sep. 1, 1987

[54] DENTAL POLISHING STRIP

[75] Inventor: Ikuo Kyotani, Kitamoto, Japan

[73] Assignee: G-C Dental Industrial Corp., Tokyo, Japan

[21] Appl. No.: 777,756

[22] Filed: Sep. 19, 1985

[30] Foreign Application Priority Data

Nov. 9, 1984 [JP] Japan .................................. 59-235046

[51] Int. Cl.$^4$ .............................................. A61C 3/06
[52] U.S. Cl. ........................................ 433/142; 132/89
[58] Field of Search ......................... 433/142, 166, 20; 132/89, 93

[56] References Cited

U.S. PATENT DOCUMENTS

| 217,300 | 7/1879 | Starr | 433/142 |
| 3,491,776 | 1/1970 | Fleming | 132/89 |
| 4,271,854 | 6/1981 | Bengtsson | 132/89 |
| 4,490,112 | 12/1984 | Tanaka et al. | 433/20 |

Primary Examiner—Robert P. Swiatek
Assistant Examiner—Adriene J. Lepiane
Attorney, Agent, or Firm—Oblon, Fisher, Spivak, McClelland, & Maier

[57] ABSTRACT

A dental polishing strip includes a substrate formed of a shape-memory alloy which is not harmful in the human mouth and is restored to the stored shape at a temperature of no lower than 40° C. for sterilization in dental clinics. The polishing strip is provided with a number of small holes, files, abrasive grains, or a combination thereof to form a polishing surface.

12 Claims, 5 Drawing Figures

DENTAL POLISHING STRIP

FIELD OF THE INVENTION

The present invention relates to improvements in a polishing strip designed to be used when dentists polish the proximal surface of a tooth of a patient or a filling in the proximal cavity.

BACKGROUND OF THE INVENTION

When dentists polish the proximal surface of a tooth of a patient or a filling in the proximal cavity for odontotherapy in a state where polishing instruments such as points, bars, disks, etc. are attached to a dental hand piece, they generally use a dental polishing strip, if there is a possibility that the teeth adjacent to the tooth to be treated may be damaged. The dental polishing strip has generally compacted abrasive grains to form a polishing surface on one side of a narrow foil-like substrate which is 2 to 5 mm in width, 120 to 180 mm in length and under 0.09 mm in thickness. For polishing, the strip is gradually inserted in the interdental space to allow the polishing surface to come in contact with the proximal surface of a tooth to be polished or a filling in the proximal cavity. Then, the strip is reciprocated vertically with respect to the longitudinal direction of the tooth. The materials of dental polishing strips are generally separated into two types, one the strips made of synthetic resins and the other the type being made of metals.

Referring to the dental polishing type being made of synthetic resins, polishing abrasive grains are compacted on a synthetic resin substrate with the use of adhesives to form a polishing surface. However, due to the fact that they are rich in flexibility but poor in strength, they have the disadvantages that the abrasive grains separate off, or the substrate per se extends with a drop of cutting force, during polishing. Furthermore, since they are less resistant to heat, they cannot be sterilized by heating for repeated use. Thus, they are used only once and should be thrown away.

On the other hand, the dental polishing strips made of metals are of three types. Referring to the first type, polishing abrasive grains are compacted on a substrate formed of stainless steel or steel to form a polishing surface. According to the second type, a number of small holes are formed in a substrate without recourse to any abrasive grains to form a polishing surface. According to the third type, a substrate is formed like a file on its surface to form a polishing surface. In the case of the first type strip, the substrate per se does not extend, and is fixedly provided with the abrasive grains, so that only slight separation thereof takes place, and high cutting force is maintained. All the first, second and third type polishing strips undergo neither tarnish nor deformation due to cleaning and heating sterilization, and so have excellent durability. Thus, the metal-made polishing strips can repeatedly be used by cleaning and heating sterilization.

However, when the metal-made dental polishing strips are repeatedly used to polish the proximal surfaces of teeth or fillings in the proximal cavity, polishing occurs along the curved planes of teeth or fillings, so that they are curved, as illustrated in FIG. 3. For that reason, difficulty is involved in inserting them into the interdentium for re-use. Furthermore, even upon sterilized by heating, they give a patient an unsanitary impression that they are much used. In addition, the metal-made strips deform to varied forms, and are so hard to arrange at the time of storage. It is thus difficult to select a proper one of the desired roughness from several types of polishing strips that are irregularly arranged. It is possible to solve the problems resulting from the appearance and manipulation of the metal-made strips by manually putting the curved strips to a straight state before use. However, this work is very troublesome to dentists. Alternatively, if the metal-made strips are substituted with new ones while the old ones are still useable, this solution suffers from an economical problem.

OBJECT OF THE INVENTION

The object of the present invention is to solve the manipulation, appearance and economical problems of the aforesaid metal-made dental polishing strips.

SUMMARY OF THE INVENTION

The present invention provides a dental polishing strip characterized in that a substarate is formed of a shape-memory alloy in place of currently available stainless steel or steel.

BRIEF DESCRIPTION OF THE DRAWINGS

The aforesaid and other objects and features of the present invention will become apparent from the following detailed description with reference to the accompanying drawings, which are given for the purpose of illustration alone, and in which.

PREFERRED EMBODIMENT OF THE INVENTION

Figure 1:
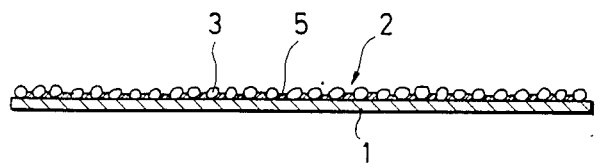
FIG. 1 is a sectional view illustrating a first embodiment of the dental polishing strip according to the present invention, in which the substrate is fixedly provided with polishing abrasive grains to form a polishing surface.
Figure 4:
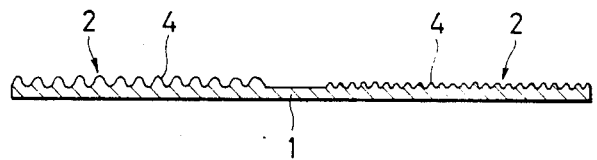
FIG. 4 is a sectional view illustrating a second embodiment of the dental polishing strip according to the present invention, in which the substrate is formed like a file on one side to form a polishing surface.
Figure 5:
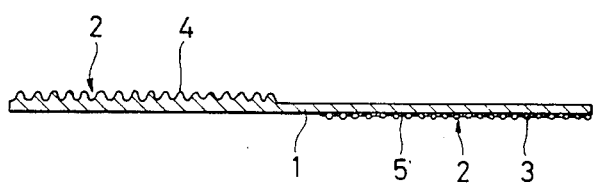
FIG. 5 is a sectional view illustrating a third embodiment of the dental polishing strip according to the present invention, in which the substrate is fixedly provided on one side from one end thereof with polishing abrasive grains, and is formed like a file on the other side from the other end thereof.

In the drawings, reference numeral 1 stands for a substrate of a polishing strip which comprises a Ti-Ni shape memory allow. The alloy is restored to the memorized shape upon exposure to a given temperature. The alloy previously stores such a straight shape as illustrated in FIG. 1 or FIGS. 4 or 5. It is desired that, as the shape-memory alloy used for the substrate 1, use be made of an alloy that is not tarnished in the human mouth, gives no harmful influence upon the human body, and is restored to the stored shape in a range of a temperature (40° C.) slightly higher than that in the human mouth (about 37° C.) to a temperature at which the sterilization used in dental clinics [such as, for instance, gas sterilization (55° C.), boiling sterilization (100° C.), high-pressure steam sterilization (121°–132° C.) or dry-heat sterilization (200°–250° C.)] can be used as such. In other words, the use of a shape-memory alloy which is restored to the stored straight shape at up to the temperature in the human mouth (about 37° C.) deteriorates considerably the manipulation properties, since a force for restoring it to the straight shape is constantly exerted during polishing of the proximal surface of a tooth or a filling in the proximal cavity. In particular, there is a possibility that the mouth of a human infant may be damaged. This is because it is desired that the minimum temperature at which the alloy is permitted to be restored to the previously stored straight shape be 40° C., taking a slight margin into consideration. It is desired that a practical temperature, at which the alloy is restored to the previously stored straight shape as illustrated in FIGS. 1, 4 or 5, and which varies depending upon the type of sterilization used, be 40°–55° C. in the case of using a gas sterilizer in the gas sterilization using an ethylene oxide gas, 40°–100° C. in the case of using a boiling sterilizer in the boiling sterilization, 40°–132° C. in the case of using an autoclave in the high-pressure steam sterilization, and 40°–250° C. in the case of using a dry-heat sterilizer in the dry-heat sterilization.

Figure 2:
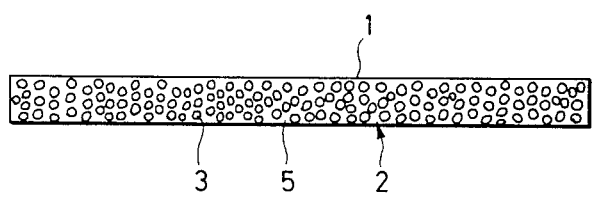
FIG. 2 is a plane view of the embodiment of FIG. 1.
Figure 3:
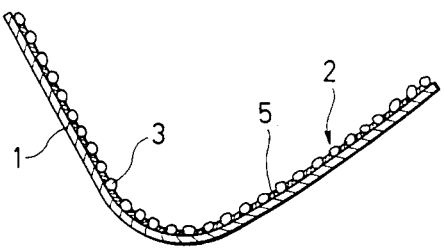
FIG. 3 is a sectional view illustrating a used-up dental polishing strip which is put in a curved state.

The alloys used as the shape-memory alloys may include Cu-Zn-Al alloys and Fe-Mn alloys in addition to the aforesaid Ti-Ni alloys. Reference numeral 2 stands for a polishing surface for polishing the proximal surface of a tooth or a filling in the proximal cavity. As shown in FIG. 2, the polishing surface 2 may be formed on one side of the substrate 1 with the same roughness. As illustrated in FIG. 4, the polishing surface 2 may have different roughness at half portions thereof. As shown in FIG. 5, to form the polishing surface 2, the substrate 1 may be provided on both sides of the middle portion thereof with different surfaces.

The polishing surface 2 may be formed by fixedly providing polishing abrasive grains 3 on the substrate 1, as illustrated in FIG. 1. Alternatively, the polishing surface 2 may have the surface of roughness 4 formed like a file at the surface of the substrate 1, as depicted in FIG. 4. Still alternatively, the polishing surface 2 may be formed by providing a number of small holes, each being 0.5 to 1.5 mm in diameter, in the substrate 1. Furthermore, the polishing surface 2 may be formed by fixedly providing polishing abrasive grains 3 on the substrate 1 with a number of small holes. Furthermore, the polishing surface 2 may have the surface of roughness 4 with a number of small holes. In the present invention, the combinations of five polishing surfaces, as mentioned above, may be used.

FIG. 1 shows the embodiment of the substrate 1 in which the polishing surface 2 is formed by fixedly providng the polishing abrasive grains 3 thereon with the use of adhesives 5. For the purpose of fixing, however, electroplating or brazing as used in the prior art may also be relied upon.

The polishing abrasive grains 3 used for the polishing surface 2 may include hard grains such as aluminium oxide, diamond, carborundum, cubic boron nitride, ceramic materials based on TiC, ZrO2 and Si3N4, or the like, the grains have a grain size of about 7–150 microns. Other abrasive grains used for conventional dental polishing strips may also be employed.

The dental polishing strip of the present invention is used in the same manner as in the prior art polishing strip. It is removed from the predetermined storage place, and it is inserted in the interdentium of a patient for the polishing of the proximal surface of his or her tooth or a filling in the proximal cavity. Thereafter, that strip is cleaned and sterilized at a given temperature for a given period of time in a gas sterilizer (in the case of gas sterilization), a boiling sterilizer (in the case of boiling sterilization), an autoclave (in the case of high-pressure steam sterilization), or a dry-heat sterilizer (in the case of a dry-heat sterilizer). In such a simple manner, that strip is restored to the shape stored in the shape-memory alloy by the temperature at which sterilization is carried out.

The dental polishing strip of the present invention is free from the problems the prior art polishing strip poses in connection with the manipulation and appearance. The invented polishing strip is designed to be restored to the straight shape at the temperature at which gas or heating sterilization is carried out, so that it can be used as a new one without giving an unsanitary feeling to a patient and with no need of carrying out troublesome work to dentists. When in storage, the polishing strips of the present invention are restored to the same shape as new ones, so that they are easily arranged. It is thus easy to select the strip having the desired roughness from the storage place.

What is claimed is:
1. A dental polishing strip comprising:
    (a) a substrate formed of a shape-memory alloy selected so that, after deformation by contact with the teeth during use, said substrate returns to its original shape upon being heated to a temperature at least slightly higher than the temperature of human mouths and
    (b) a polishing surface on said substrate for polishing the proximal surfaces of teeth or fillings in the proximal cavity.
2. A dental polishing strip as recited in claim 1 wherein said shape-memory alloy is selected so that, after deformation by contact with the teeth during use, said substrate returns to its original shape upon being heated to a temperature in the range of 40° C. to 250° C.
3. A dental polishing strip as recited in claim 1 wherein said shape-memory alloy is selected from the group consisting of Ti-Ni shape-memory alloy, Cu-Zn-Al shape-memory alloy, and Fe-Mn shape-memory alloy.
4. A dental polishing strip as recited in claim 1 wherein said polishing surface is formed like a file.
5. A dental polishing strip as recited in claim 1 wherein said polishing surface is formed on one side only of said substrate.
6. A dental polishing strip as recited in claim 1 wherein said polishing surface is formed on both sides of said substrate.
7. A dental polishing strip as recited in claim 1 wherein said polishing surface is formed from polishing adhesive grains mounted on said substrate.
8. A dental polishing strip as recited in claim 7 wherein said polishing adhesive grains are selected from the group consisting of aluminum oxide, diamond, carborundum, cubic boron nitride, and ceramic materials based on TiC, $ZrO_2$, or $Si_3N_4$.
9. A dental polishing strip as recited in claim 7 wherein said polishing adhesive grains have a grain size of about 7–150 microns.
10. A dental polishing strip as recited in claim 7 wherein said polishing adhesive grains are mounted on said substrate by means of an adhesive.
11. A dental polishing strip as recited in claim 7 wherein said polishing adhesive grains are mounted on said substrate by means of electroplating.
12. A dental polishing strip as recited in claim 7 wherein said polishing adhesive grains are mounted on said substrate by means of brazing.

* * * * *